United States Patent [19]

Takezono et al.

[11] 4,256,465
[45] Mar. 17, 1981

[54] METHOD FOR PRODUCING METHYL TERT-BUTYL ETHER AND FUEL COMPOSITION CONTAINING THE SAME

[75] Inventors: Tetsuya Takezono, Kawasaki; Yasuo Fujiwara, Tokyo, both of Japan

[73] Assignee: Nippon Oil Co., Ltd., Tokyo, Japan

[21] Appl. No.: 59,377

[22] Filed: Jul. 20, 1979

Related U.S. Application Data

[62] Division of Ser. No. 853,192, Nov. 21, 1977, Pat. No. 4,182,913.

[30] Foreign Application Priority Data

Nov. 22, 1976 [JP] Japan ................ 51-140479
Nov. 22, 1976 [JP] Japan ................ 51-140480
Oct. 14, 1977 [JP] Japan ................ 52-123154

[51] Int. Cl.³ .......................................... C10L 1/02
[52] U.S. Cl. .................................. 44/56; 568/697; 568/689
[58] Field of Search .................... 44/56; 260/614; 568/697; 853/192

[56] References Cited

U.S. PATENT DOCUMENTS

| | | | |
|---|---|---|---|
| 2,839,569 | 6/1958 | Kramer | 260/615 R |
| 2,855,437 | 10/1958 | Lyons | 260/616 X |
| 2,958,626 | 11/1960 | Schenck et al. | 423/600 |
| 3,539,306 | 11/1970 | Kumura et al. | 423/432 |
| 3,920,582 | 11/1975 | Roma | 260/614 R |
| 3,940,450 | 2/1976 | Lee | 260/614 A |
| 4,039,590 | 8/1977 | Analotte et al. | 260/614 A |

FOREIGN PATENT DOCUMENTS 2707765 9/1977 Fed. Rep. of Germany ...... 260/614 A
957000 4/1964 United Kingdom ................ 260/614 A

OTHER PUBLICATIONS

Kaiser et al., I & EC Product Research & Development, vol. 1, 1962, pp. 296-302.
Merck Index, 9th Ed., Merck & Co., Rahway, N.J., 1976, #5483, p. 737.

*Primary Examiner*—Winston A. Douglas
*Assistant Examiner*—Y. Harris-Smith
*Attorney, Agent, or Firm*—Ostrolenk, Faber, Gerb & Soffen

[57] ABSTRACT

A method for producing methyl tert-butyl ether which comprises the steps of: allowing isobutylene-containing hydrocarbon and methyl alcohol in a given molar ratio to react at a given temperature, pressure and liquid space velocity in the presence of strongly acidic cation-exchange resin catalyst; then passing the reaction product through a fixed bed filled with a water-insoluble, solid particulate acid-neutralizing agent; and subjecting the effluent to flashing operation, preferably also to rectification, to obtain methyl tert-butyl ether. Further included in the invention is the preparation of a fuel composition by mixing the thus obtained methyl tert-butyl ether into an internal combustion fuel.

7 Claims, 1 Drawing Figure

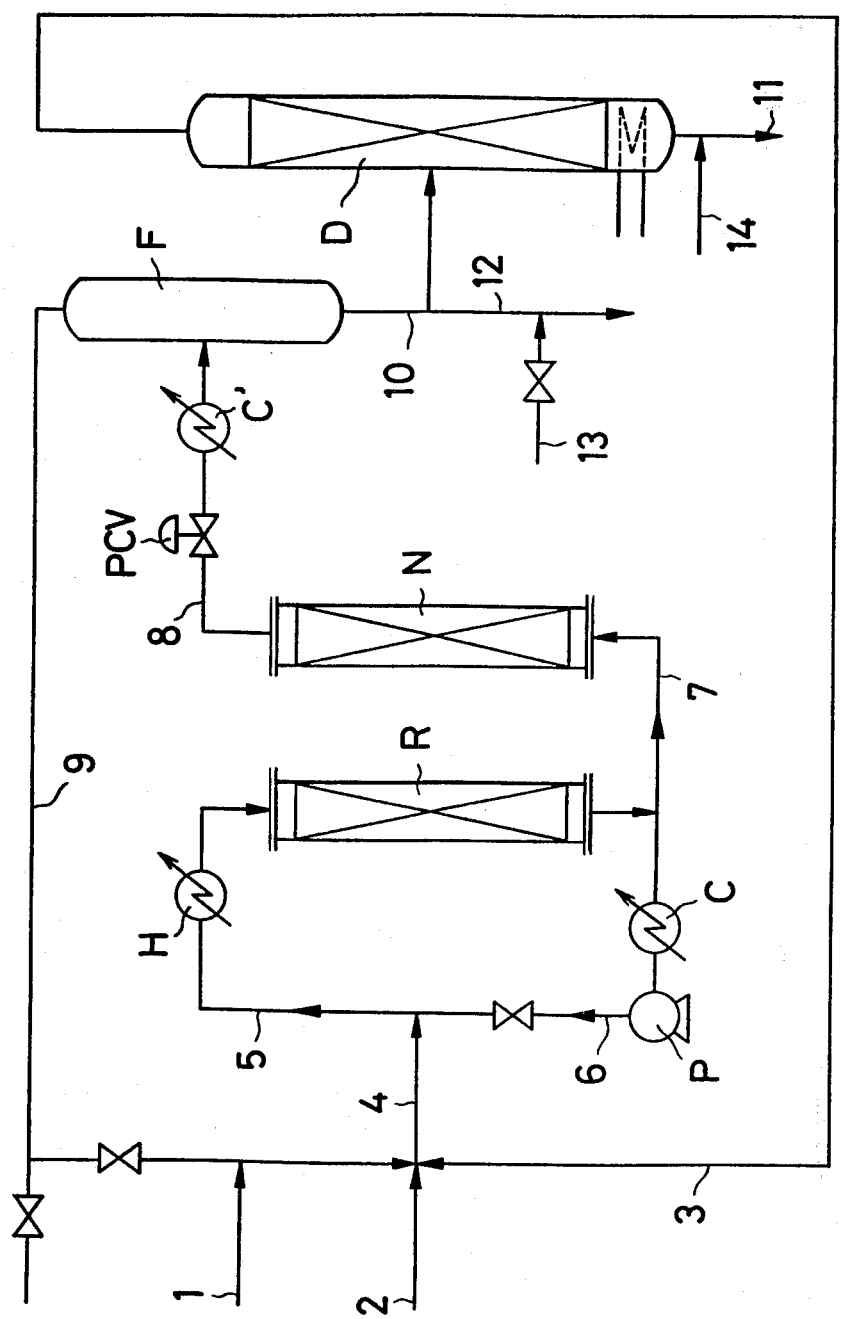

METHOD FOR PRODUCING METHYL TERT-BUTYL ETHER AND FUEL COMPOSITION CONTAINING THE SAME

This is a division of application Ser. No. 853,192, filed Nov. 21, 1977, now U.S. Pat. No. 4,182,913.

BACKGROUND OF THE INVENTION

This invention relates to a method for continuously producing methyl tert-butyl ether in high yield by allowing an isobutylene-containing hydrocarbon mixture and methyl alcohol to react with each other in the presence of a catalyst. This invention further relates to the preparation of a fuel composition which is made by mixing the thus obtained methyl tert-butyl ether into an internal combustion fuel.

In recent years, there has arisen a social problem of environmental pollution with lead which is caused by the exhaust gases of internal combustion engines. As a result, regular gasoline has already been made lead-free completely and premium gasoline will also be made lead-free in due course. Hence, in order to produce unleaded gasoline while maintaining octane value as in the past and without varying the compounding ratio of basic gasoline, an octane value improving agent must be added to gasoline.

There are known many kinds of compounds as the octane value improving agents. Particularly, ethers having branched alkyl groups are well known as they have been disclosed in the Third World Petroleum Congress, Sec. VI, 397 (1951). For example, it is well known that the octane values of methyl tert-butyl ether (hereinafter referred to as "MTBE"), ethyl tert-butyl ether and isopropyl tert-butyl ether are very high.

With regard to the method for producing MTBE, it is known that MTBE is prepared by the reaction between methyl alcohol and isobutylene in the presence of a catalyst. Especially, proposed in some methods is the use of strongly acidic cation-exchange resin as a catalyst (cf. Japanese Patent Publication No. 34803 of 1973, Japanese Patent Laid-open Publication No. 61109 of 1974, Japanese Patent Laid-open Publication No. 58006 of 1975, and U.S. Pat. No. 2,480,940). In these conventional methods, however, an acid substance is extruded from the strongly acidic cation-exchange resin during the reaction so that the reaction mixture is accompanied by the acid substance. In addition, since the succeeding separation step of distillation is done with heating, the reverse reaction from MTBE to methyl alcohol and isobutylene is caused to occur as the MTBE has tertiary carbon atoms. Accordingly, the yield of MTBE is disadvantageously reduced. Further, the reaction product containing such acid substance cannot be mixed into fuel oil as it stands.

BRIEF SUMMARY OF THE INVENTION

It is, therefore, the object of the present invention to eliminate the above-described disadvantages in the conventional art and to provide a novel and industrially serviceable method for producing MTBE which can be mixed into fuel oil.

Another object of the present invention is to provide a method for preparing a fuel composition for internal combustion engines which is made by mixing the above MTBE into internal combustion fuel.

According to the present invention, a mixture of isobutylene-containing hydrocarbon mixture and methyl alcohol at a molar ratio (isobutylene: methyl alcohol) of 1:0.6 to 1:1.4, is used. The above mixture is passed through a fixed bed which is filled with the particles of strongly acidic cation-exchange resin at a temperature in the range of 0° to 100° C., a liquid space velocity of 0.1 to 50 (1/hr) and a pressure of 1 to 50 atms. The above strongly acidic cation-exchange resin has a mean grain diameter of 0.2 to 10 mm. The reaction mixture obtained through the resin bed is then passed through a fixed bed filled with a water-insoluble solid particulate acid-neutralizing agent having a mean grain diameter of 0.1 to 10 mm at a temperature of 0° to 100° C. The reaction mixture is further introduced into a flashing tower so as to flash-removal unchanged hydrocarbon, thereby obtaining a mixture containing MTBE from the bottom of the flashing tower.

According to another aspect of the present invention, the above mixture containing MTBE is further subjected to distillation in a multi-stage distillation column, thereby continuously obtaining MTBE from the bottom of the distillation column and an azeotropic mixture of MTBE and methyl alcohol from the top of the column, which azeotropic mixture is then recycled to the initial reaction vessel of the cationexchange resin tower.

According to still a further aspect of the present invention, a fuel composition for internal combustion engines is prepared by mixing 2 to 30% by volume of the above obtained MTBE or MTBE-containing mixture into internal combustion fuel.

BRIEF DESCRIPTION OF THE DRAWING

For a fuller understanding of the invention, reference is had to the following description taken in connection with the accompanying drawing, in which:

The single FIGURE is a flow diagram of the process in accordance with the present invention.

DETAILED DESCRIPTION OF THE INVENTION

In the method of the present invention, isobutylene-containing hydrocarbon and methyl alcohol are employed as starting materials. As the isobutylene-containing hydrocarbon, pure isobutylene itself is of course used, however, hydrocarbon mixtures containing isobutylene may also be used. That is, such mixtures may contain, in addition to isobutylene, n-butane, isobutane, butene-1, butene-2 and butadiene. For example, the $C_4$ fractions which are obtained by thermal cracking, steam cracking and catalytic cracking can be conveniently used. As the methyl alcohol, commercially available ones can be used, while it is desirable that methyl alcohol contains not more than 1% of water.

When isobutylene-containing hydrocarbon and methyl alcohol are fed into the catalyst bed of strongly acidic cation-exchange resin, they are heated separately or in a mixture near to the reaction temperature. In this step, the unreacted isobutylene-containing hydrocarbon distilled out from the top of flashing tower (described later) or the azeotropic mixture of MTBE and methyl alcohol obtained from the top of final distillation column or refining column (described later) can be recycled and mixed into the above raw material line. The mixture of raw materials such as newly fed methyl alcohol, isobutylene or isobutylene-containing hydrocarbon, the above-mentioned azeotropic mixture and the isobutylene distillate from the flashing tower are, as a whole, hereinafter referred to as "raw material system" which is to be introduced into a reaction vessel. The molar ratio (isobutylene: methyl alcohol) in the raw material system is in the range of 1:0.6 to 1:1.4. In the case that the molar ratio is smaller than 0.6, isobutylene exists in too much excess and unreacted isobutylene and isobutylene dimer increase. Especially when the butane-butene fraction obtained in naphtha cracking is used as the isobutylene material, the rate of reaction of isobutylene must be raised as high as possible in view of the utilization of $C_4'$-1 and $C_4'$-2 in the unreacted butane-butene fraction, so that a small molar ratio is not preferable. The minimum value of this molar ratio is preferably 0.75.

On the other hand, if the above molar ratio is larger than 1.4, the unreacted methyl alcohol becomes large. Accordingly, the methyl alcohol content in the MTBE-containing mixture from the bottom of flashing tower becomes large or the quantity of azeotropic mixture that is obtained from the top of refining tower and recycled to the raw material system, becomes large. Therefore, the output of MTBE will be reduced. In other words, since the azeotropic composition of MTBE to methyl alcohol is 85:15 by weight, when the quantity of unreacted methyl alcohol increases, the quantity of MTBE in the azeotropic mixture increases as a matter of course, and accordingly, the MTBE product obtained from the bottom of the column becomes small. The quantity of MTBE in the azeotropic mixture that is recycled into the raw material system is at most 50% of the MTBE that has been produced by reaction. When such percentage of MTBE exceeds 50%, the process becomes uneconomical. The molar ratio at this critical condition is 1.4, however, the molar ratio is preferably not more than 1.3.

The strongly acidic cation-exchange resins used in the method of the present invention are cation-exchange resins which have strongly acidic property and are represented by styrene sulfonic acid type ones and phenol sulfonic acid type ones. The styrene sulfonic acid type ion exchange resin is prepared by copolymerizing the poly-unsaturated compounds such as styrene and divinylbenzene and sulfonating the obtained resin, which product is represented by the general formula:

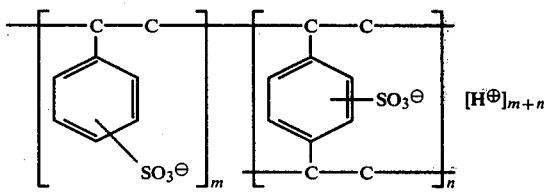

in which the symbols m and n are positive integers.

The phenol sulfonic acid type resin is ordinarily a condensate of phenol sulfonic acid with formaldehyde and is represented by the following general formula:

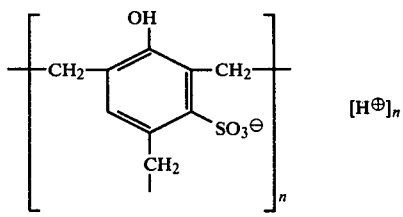

in which the symbol n is a positive integer.

The above-mentioned strongly acidic cation-exchange resins are used as catalyst in the method of the present invention. The mean grain diameter of the cation-exchange resin is in the range of 0.2 to 10 mm and the shape of each resin particle is spherical or columnar.

The particles of catalyst are charged in a pressure resistant cylindrical reaction vessel, thereby forming a fixed bed reactor.

The size of the fixed bed is not restricted and it is ordinarily in the range of 0.2 m to 20 m in height. It is possible to use a plurality of fixed beds arranged in series or parallel relationship to one another.

The foregoing methyl alcohol and isobutylene are continuously fed into the fixed bed from the top or bottom, preferably from the top, thereof. The feeding quantity of them is in the range of 0.1 to 50 ($m^3/m^3 \times 1/hr = 1/hr$), and preferably from 0.5 to 15 (1/hr), in liquid space velocity. The liquid space velocity herein referred to is the sum in volume ($m^3$) of newly fed isobutylene, methyl alcohol, the isobutylene recovered from the flashing step and the azeotropic mixture of MTBE and methyl alcohol recycled from the top of a refining tower per hour and cubic meter of catalyst, measured at 20° C. and 2.5 kg/cm².

When the liquid space velocity of the raw materials to be reacted is smaller than 0.1 (1/hr), even though the reaction proceeds sufficiently, the quantity of reaction product is small so that it is unfavorable to industrial practice, and in addition, the decomposition of reaction product increases. On the other hand, when the liquid space velocity exceeds 50 (1/hr), the reaction proceeds insufficiently and the load to the succeeding refining process becomes large disadvantageously.

In the reaction, inert solvents, particularly inert hydrocarbon solvents, can be used. For example, the $C_4$ hydrocarbon fraction obtained in naphtha cracking or the butane-butene fraction which is obtained by separating butadiene from the $C_4$ hydrocarbon fraction, can be used as it stands as the isobutylene source.

When methyl alcohol and isobutylene are passed through the fixed bed in the method of the present invention, the reaction mixture obtained from the fixed bed may be divided into two parts. One part is then supplied into the fixed bed that is filled with acid-neutralizing agent, and the other part is directly recycled into the fixed bed that is filled with the ion exchange resin. In this case, the quantity of the latter portion to be recycled may be 3 to 15 parts by weight per 1 part of the former portion to be supplied to the succeeding step.

In this connection, the liquid space velocity representing the quantity of starting materials being fed, is independent of the quantity of the mixture which is to be recycled directly to the first reaction vessel as set forth in the above.

The reasons why the recycle-feeding system is adopted in the process of the present invention are as follows. The reaction between methyl alcohol and isobutylene is exothermic, and because of the nature of catalyst used in the process of the invention, it is necessary to maintain the temperature in the reactor constant. Particularly, the rise in temperature to excess must be strictly avoided from the viewpoint of the prevention of subsidiary reaction and deterioration of catalyst.

In the case that the recycle system is not employed, the difference in temperature between the inlet and the outlet of the reaction vessel becomes large so that the reaction vessel must be provided with a special cooling means. However, the coefficient of heat transfer of the ion exchange resin is low, so that the reaction vessel must be made shell-and-tube type or the like, with which the change of used ion exchange resin in the reaction bed becomes difficult and troublesome. Further, even when such reaction vessel is used, the occurrence of local high temperature portions cannot still be avoided. When the recycling system is employed, the temperature in the reaction bed can well be maintained evenly.

The reaction pressure in the process of the present invention is maintained within the range of 1 to 50 atms, preferably 5 to 30 atms. In the case that the reaction pressure is lower than 1 atm, incomplete reaction will result. While, if the reaction pressure exceeds 50 atms, the reaction vessels and their accessory devices must be made pressure-resistant, which is disadvantageous from economical and industrial viewpoint.

The reaction temperature in the process of the present invention falls within the range of 0° C. to 100° C. When the reaction temperature is lower than 0° C., the reaction does not proceed sufficiently. If the reaction temperature is set above 100° C., the side reaction such as the oligomeration of isobutylene increases, so that it is not desirable. The most preferable temperature range of the reaction is 30° C. to 70° C. Further, when the reaction temperature becomes higher, a larger quantity of acid substance is effused from the strongly acidic cation-exchange resin and the deterioration of the catalyst resin is accelerated. Even when the reaction temperature is low, a small quantity of the substance having a strongly acidic property is effused into the reaction mixture and the reaction mixture containing the acid substance is obtained from the reactor. When such a reaction mixture containing the acid substance is fed into the succeeding step of unreacted gas separation so as to separate the unreacted gas by distillation (distillation is generally accompanied by heating), the decomposition or reverse reaction of the main product is caused to occur, which reduces the yield. In addition, various portions of apparatus are corroded.

In order to remove such acid substance, it may be considered to neutralize by adding an aqueous solution of a strongly basic substance such as sodium hydroxide or calcium oxide or hydroxide, however, the removal of the salt that is generated by neutralization is difficult. Further, it is difficult to control the quantity of basic substance to be added because the concentration of the acid substance is varied considerably according to the kind of catalyst, the quantity of supplied raw materials, reaction temperature, reaction time and so forth. When the quantity of basic substance is too small, the acid substance cannot be neutralized completely so that the above-mentioned drawbacks still remains, while if the basic substance is too much, the succeeding step to remove unreacted gas must be carried out under the conditions to treat strongly basic substance. Further, it is quite inconvenient that the product must be washed with water and distilled before it is mixed into internal combustion fuel.

Further, when the solid sodium hydroxide or solid calcium oxide is used as it stands, the solid is dissolved in the continuous use and the disadvantages like the above are caused to occur.

Still further, it is considered that the acid substance can be removed by using an adsorbing agent such as active carbon, however, the adsorbing capacity thereof is small and, when the concentration of acid to be adsorbed is low, the acid adsorbing capacity becomes quite low.

These problems have been solved in the process of the present invention. That is, the reaction mixture obtained from methyl alcohol and isobutylene is passed through a fixed bed filled with a water-insoluble, solid particulate acid-neutralizing agent having a mean grain diameter of 0.1 to 10 mm, so that the reaction mixture and the acid-neutralizing agent are brought into contact with each other. The water-insoluble, solid particulate acid-neutralizing agent herein referred to is an inorganic solid particulate material which has a very low solubility in water (less than 0.1 g/100 g of water under the ordinary condition) and an acid-neutralizing capacity of more than 1.0 m-mole/g.

The acid-neutralizing capacity is determined by adding the solid neutralizing agent to an aqueous solution containing 1% by weight of $H_2SO_4$, allowing the above aqueous solution to stand for 10 hours at 50° C., removing the solid neutralizing agent from the solution, and calculating the number of m-mol of $H_2SO_4$ that is removed from the aqueous solution per gram of the solid neutralizing agent.

Exemplified as the water-insoluble, solid particulate acid-neutralizing agents for the process of the present invention are magnesium oxide, alumina, silica, silica-alumina, magnesium-aluminium double oxide and its hydrate, and double oxides of magnesium and/or aluminium with at least one member selected from the group consisting of Na, K, C, Si, Ca, Ba and Sr, and their hydrates, which are exemplified by the chemical formulae: MgO, MgO.$mH_2O$ (m=0–0.5), $Al_2O_3$, hydrotalcite (6MgO.$Al_2O_3$.$CO_2$12$H_2O$), $Al_2O_3$.$mSiO_2$.$nH_2O$ (m=0.5–3, n=1–6), $Al_2O_3$.$nH_2O$, 2.5MgO.$Al_2O_3$.$nH_2O$, $Na_2O$.$Al_2O_3$.$nH_2O$ and 2MgO.6$SiO_2$.$nH_2O$ (each n=1–6).

Among these compounds, the hydrotalcite and MgO are advantageously used in the process of the present invention. The hydrotalcite herein referred to is generally natural one having a molar ratio (magnesium to aluminium) of about 3. In the case that the hydrotalcite is a synthesized one, the molar ratio of magnesium to aluminium thereof may cover a wide range depending upon the production process. Some of the hydrotalcites having a molar ratio of magnesium to aluminium ranging from 1 to 10 show an X-ray diffraction diagram having a peak which features the hydrotalcite whose molar ratio of magnesium to aluminium is approximately 3. Therefore, those having a molar ratio of 1 to 10 in magnesium to aluminium are included in the hydrotalcites as referred to in the present invention and they are effectively used in the present invention.

The foregoing solid, particulate acid-neutralizing agents are spherical, flake- or columnar-shape and have mean grain diameters in the range of 0.1 to 10 mm. When they are used, they are filled in vessels to form fixed beds.

The above-described reaction mixture is continuously passed through a fixed bed of neutralization at a temperature in the range of 0° to 100° C. When the treating temperature is made below 0° C., not only the acid substance is removed insufficiently but also the heat loss increases since the reaction mixture from the reactor must be previously cooled. When the temperature is higher than 100° C., the reaction mixture from the reactor must be preheated which results in the loss of heat. The preferable temperature of the treatment is set near to the reaction temperature. That is, the reaction mixture may be fed into the neutralizing bed from the outlet of reaction vessel with the spontaneous cooling in transferring lines. The quantity of reaction mixture to be fed into the fixed bed is generally in the range of 0.1 to 20 (1/hr) in liquid space velocity.

In the process of the present invention, the reaction mixture is then introduced into a flashing tower to carry out flashing treatment. The flashing tower is normally a multi-stage tower, with which the unreacted hydrocarbons (those contained in unreacted isobutylene and isobutylene-containing hydrocarbon) are separated out of the top of the tower. In this operation, two or three flashing towers may be arranged in series relation so as to be used as a multi-stage tower. The isobutylene thus separated is liquefied and then it may be recycled to the initial reaction vessel.

From the bottom of the flashing tower, a mixture containing MTBE is recovered. This mixture contains MTBE as the main component and a little quantity of unreacted methyl alcohol. The MTBE referred to in the present invention includes this MTBE-containing mixture and it can be used for preparing the fuel composition for internal combustion engines.

Further, in order to reduce the content of methyl alcohol in the MTBE-containing mixture as low as possible, this mixture is fed into the succeeding refining tower and distilled therein. From the top of the tower is obtained an azeotropic mixture of both MTBE and methyl alcohol, and from the bottom of the tower, purer MTBE can be recovered relationship. According to the conditions of distillation with the refining tower, the methyl alcohol content in the recovered MTBE can be varied. With ordinary operation of distillation, the methyl alcohol content can be reduced to the level lower than 0.5% without difficulty. Further, the content of isobutylene dimer as by-product in this product MTBE is very small. This is due to the fact that in the reaction of this invention, the quantity of isobutylene is not too much in excess in view of the moles of methyl alcohol. In the preferably adopted reaction condition, the molar ratio of isobutylene:methyl alcohol is in the range of 1:1.0 to 1:1.4, and more preferably, 1:1.0 to 1:1.3. With this reaction condition, it is easy to reduce the content of isobutylene dimer to a level lower than 0.5%. The azeotropic mixture that is obtained from the top of refining tower has a composition of methyl alcohol:MTBE=1:5.7 (by weight), however, those having a composition in the range of methyl alcohol:MTBE =1:5.4 to 1:6.0 are herein referred to as "azeotropic mixture". The effective reuse of methyl alcohol by recycling this azeotropic mixture into the raw material system, constitutes one of characteristic features of the present invention.

The advantages in the present invention are as follows. The methyl alcohol content in MTBE recovered from the bottom of refining tower can be reduced. Further, as described above, since the reaction is carried out under the condition that the moles of methyl alcohol are larger than that of isobutylene, the rate of reaction of isobutylene can be raised and the quantity of by-product diisobutylene can be reduced.

Further, since the azeotropic mixture of MTBE and methyl alcohol obtained from the multi-stage distillation tower is recycled, it is not necessary to separate and remove the unreacted methyl alcohol from the product MTBE by washing the reaction product with water, and highly pure MTBE can be recovered from the bottom of the tower. In the case that the unreacted methyl alcohol is removed by water washing, it is economically undesirable to discard the unreacted methyl alcohol, while the water in the methyl alcohol must be removed in order to reuse the methyl alcohol. In accordance with the process of the present invention, MTBE can be advantageously produced without the necessity of discarding or drying of the recovered methyl alcohol.

Further, in the other aspect of the process of the present invention, a fuel composition for internal combustion engine is prepared by mixing 2 to 30% by volume, preferably 5 to 20% by volume, of the above-described MTBE-containing mixture or MTBE obtained from the bottom of the refining tower, into internal combustion fuel. In the present invention, it is one of great advantages that the fuel composition for internal combustion engine can be prepared by adding the above MTBE-containing mixture or MTBE as it stands into internal combustion fuel. The manner for mixing is not especially restricted and both the materials are simply mixed together. Exemplified as the preferable internal combustion fuels are the fractions obtained by distilling synthetic or natural petroleum, hydrocarbons boiling in the gasoline range that are prepared by cracking or reforming the above fractions, alcohols having 1 to 4 carbon atoms such as methyl alcohol and isopropyl alcohol, and ethers having 4 to 8 carbon atoms such as methyl isopropyl ether, methyl tert-butyl ether, isopropyl tert-butyl ether and their mixtures. Particularly, when 2 to 30% by volume of the above MTBE or MTBE-containing mixture is added to motor gasoline, the octane value of the obtained fuel composition is increased and the exhaust gas therefrom contains little nitrogen oxides. The basic gasoline for the preparation of the fuel composition is exemplified by straight gasoline, cracked gasoline, catalytically cracked gasoline and catalytically reformed gasoline, and the mixture of two or more of them. Further, the fuel composition of the invention may be combined with several additives which are used for the conventional fuel oils.

In order to describe the process of the present invention in more detail, an exemplarly process will be illustrated with reference to the accompanying flow sheet.

A raw material, isobutylene, is fed through a pipeline 1 and another raw material, methyl alcohol, is fed through a pipeline 2. The azeotropic mixture that has been obtained from the top of a refining tower D for the final product MTBE, is fed into the new raw material system through a pipeline 3. If necessary, recovered unreacted isobutylene (described later) is also added to the raw material system through a pipeline 9. The mixture of raw materials is fed into a heater H through pipelines 4 and 5 and heated to a given temperature, and it is further introduced into a fixed bed reaction tower R which is filled with particles of strongly acidic cation-exchange resin. The fluid taken out from the reaction tower R is divided into two parts, one part is cooled by a cooler C and recycled by a circulation pump P and through a pipeline 6 into the stream of the raw material system from the pipeline 4, which is fed into the reaction tower R. In the case that the recycling is not done in the process of the present invention, the pipeline 6 is not used. The other part of fluid from the reaction tower R is fed into a fixed bed neutralizing tower N through a pipeline 7. The neutralizing tower N is filled with a water-insoluble, solid particulate acid-neutralizing agent. The pressures of the reaction tower R and the neutralizing tower N are controlled to given pressures by a pressure controlling valve PCV. The fluid taken out from the neutralizing tower N is passed through a pipeline 8 and the pressure of the fluid is then reduced by the valve PCV, and then the temperature of the fluid is controlled by a heat exchanger C' to be fed into a flashing tower F. A hydrocarbon mixture containing unreacted isobutylene is discharged from the top of the flashing tower F and through a pipeline 9. When the hydrocarbon mixture is reused, it is liquefied and combined with the raw material isobutylene in the pipeline 1. The MTBE-containing mixture obtained from the bottom of the flashing tower F is an aimed MTBE in the process of the present invention, which is taken out from a pipeline 12. Further, this flow of MTBE-containing mixture can be fed into a refining tower D through a pipeline 10. The fluid (azeotropic mixture) taken out from the top of the refining tower D is, as described above, fed into the raw material system through the pipeline 3. A high purity MTBE product is obtained from the bottom of the refining tower D through a pipeline 11.

Further, the MTBE-containing mixture obtained from the bottom of the flashing tower F through the pipeline 12 or the MTBE product obtained from the pipeline 11 is mixed at a given ratio with the internal combustion fuel which is transferred through a pipeline 13 or 14.

The characteristic features of the present invention will be further made clear with some examples in the following.

EXAMPLE 1

A reaction tower R was filled with 30 lit. of catalyst, styrene type ion exchange resin (trademark: Amberlyst 15 having a mean grain diameter of 0.5 mm, a product of Rohm and Haas Company). A neutralizing tower N was filled with 20 lit. of hydrotalcite ($6MgO.Al_2O_3.CO_2.12H_2O$) having a mean grain diameter of 0.7 mm). Isobutylene (Purity: 99%) was fed through a pipeline 1 at a flow rate of 105.0 kg/hr and methyl alcohol (purity: 99%) was fed through a pipeline 2 at a flow rate of 58.5 kg/hr (1.83 kg·mole/hr). Unreacted isobutylene was recycled for reuse through a pipeline 9 at a flow rate of 28.3 kg/hr. Thus the flow rate of isobutylene as a whole in the pipeline 4 was 133.3 kg/hr (2.38 kg.mole/hr). The liquid space velocity of the raw materials was 10 (1/hr). The pressure in the reaction system was maintained at 15 kg/cm$^2$G with a pressure controlling valve PCV. The mixed raw materials of isobutylene and methyl alcohol were combined with the fluid from the recycled pipeline 6 and the mixture was then fed into the reaction tower R through a pipeline 5. The temperature of the inlet of reaction tower R was set to 50° C. by means of a heat exchanger H. The flow rate of the fluid in the pipeline 6 was controlled to 7 times as much as the flow rate of raw material feed through the pipeline 4, by means of a circulation pump P. The flow rate of the fluid from the reaction tower R through the pipeline 7 was 191.8 kg/hr, the fluid contained 85.2% by weight of MTBE, 14.0% by weight of unreacted isobutylene, 0.8% by weight of isobutylene dimer and 0% of unreacted methyl alcohol, and the concentration of acid in this fluid was $3.5 \times 10^{-4}$ eq/lit. The fluid was passed through the pipeline 7 into the neutralizing tower N and further through the pipeline 8 into the flashing tower F at normal pressure. Unreacted isobutylene was flashed off from the top of the flashing tower F and it was supplied into the raw material isobutylene line through the pipeline 9. From the bottom of the flashing tower F, MTBE-containing mixture of 99.1% in purity was obtained at a flow rate of 160 kg/hr. The impurity in the product was isobutylene dimer and the acid concentration was very low as $1.4 \times 10^{-7}$ eq/lit.

EXAMPLE 2

To the MTBE-containing mixture obtained in Example 1 was added 1926 lit/hr of regular gasoline through the pipeline 13, thereby obtaining a fuel composition for internal combustion engines which contained 10% by volume of MTBE-containing mixture. The research method octane value of the fuel composition was 95.

EXAMPLE 3

A reaction tower R was filled with 30 lit. of catalyst, styrene type cation-exchange resin (trademark: Amberlyst 15 having a mean grain diameter of 0.5 mm, a product of Rohm and Haas Company). A neutralizing tower N was filled with 20 lit. of hydrotalcite ($6MgO.Al_2O_3.CO_2.12H_2O$) having a mean grain diameter of 0.7 mm). Isobutylene (purity: 99%) was fed through a pipeline 1 at a flow rate of 60.7 kg/hr and methyl alcohol (purity: 99%) was fed through a pipeline 2 at a flow rate of 35.2 kg/hr. The unreacted isobutylene and azeotropic mixture were recycled for reuse respectively through the pipelines 3 and 9. Thus the flow rates through the pipeline 4 were such that: isobutylene was 62.2 kg/hr (1.11 kg·mole/hr); methyl alcohol, 46.1 kg/hr (1.44 kg·mole/hr); and MTBE, 49.3 kg/hr. The liquid space velocity in the reaction system was 7.7 (1/hr) and the pressure therein was maintained at 15 kg/cm$^2$G with the pressure controlling valve PCV. The mixture of isobutylene, methyl alcohol and MTBE was combined with the fluid from the pipeline 6 and the combined fluid was introduced into the reaction tower R through the pipeline 5. The temperature of the inlet of the reaction tower R was controlled to 50° C. by a heat exchanger H and, with the circulation pump P, the flow rate of the fluid passed through the pipe line 6 was set to 7 times as much as the flow rate of the fluid passed through the pipeline 7 (this corresponds to the sum of raw material isobutylene, methyl alcohol and MTBE). The flow rate of the fluid taken out from the reaction tower R through the pipeline 7 was 157.4 kg/hr and the fluid contained 1.0% by weight of isobutylene, 7.4% by weight of methyl alcohol and 91.6% by weight of MTBE. The fluid passed through the pipeline 7 was fed into the neutralizing tower N and the effluent of the tower N through the pipeline 8 was then fed into the flashing tower F at normal pressure. Gaseous fluid of a greater part of isobutylene was removed from the top of the flashing tower F at a flow rate of 1.5 kg/hr and it was combined into the raw material isobutylene line through the pipeline 9. From the bottom of the flashing tower F, 154.3 kg/hr of liquid containing 93.5% by weight of MTBE was obtained, which was then supplied into the refining tower D through the pipeline 10. From the top of the refining tower D, 58.3 kg/hr of an azeotropic mixture of MTBE and methyl alcohol was taken out, which was then fed into the raw material line through the pipeline 3. From the bottom of the refining tower D, 95.7 kg/hr of MTBE of 99.5% by weight in purity was taken out, in which the impurity was only methyl alcohol.

EXAMPLE 4

To the MTBE that was obtained in Example 2, 739 lit/hr of regular gasoline was mixed through the pipeline 14, thereby obtaining a fuel composition for internal combustion engines containing 15% by volume of MTBE. The research method octane value of thus prepared fuel composition was 96.

EXAMPLE 5

Styrene was polymerized with about 12% of divinylbenzene and the product was then sulfonated to obtain a catalyst having a particle size of 20 to 50 mesh. 30 lit. of this catalyst was fed into the reaction tower R. $C_4$ fraction containing 40% of isobutylene was fed through the pipeline 1 at a flow rate of 189.2 kg/hr and methyl alcohol was fed through the pipeline 2 at a flow rate of 43.4 kg/hr. An azeotropic mixture was recycled through the pipeline 3 for reuse. The flow rates of materials in the pipeline 4 were $C_4$ fraction 189.2 kg/hr (isobutylene 1.35 kg·mole/hr), methyl alcohol 46.0 kg/hr (1.44 kg·mole/hr) and MTBE 15.0 kg/hr. The liquid space velocity of the fluid therein was 13.3 (1/hr). The temperature of the inlet of the reaction tower R was controlled to 60° C. by the heat exchanger H. Other conditions were the same as those in Example 3. The flow rate of the fluid from the reaction tower R through the pipeline 7 was 250.2 kg/hr and the fluid contained 45.5% by weight of $C_4$ fraction (in which isobutylene was 0.4%), 1.2% by weight of methyl alcohol, 0.1% by weight of isobutylene dimer and 53.2% by weight of MTBE. From the top of the flashing tower F, 113.9 kg/hr of $C_4$ fraction was separated. From the bottom of the flashing tower F, 139.7 kg/hr of liquid containing 93.1% by weight of MTBE was obtained and it was then introduced into the refining tower D. From the top of the refining tower D, an azeotropic mixture of MTBE and methyl alcohol was taken out at a flow rate of 17.6 kg/hr and it was supplied into the raw material line through the pipeline 3. From the bottom of the refining tower D, MTBE of 99.4% by weight in purity was obtained at a flow rate of 118.7 kg/hr. The impurities therein were 0.4% by weight of methyl alcohol and 0.2% by weight of isobutylene dimer.

EXAMPLE 6

The MTBE that was obtained in Example 5 was mixed with 905 lit/hr of regular gasoline from the pipeline 14, thereby obtaining a fuel composition for internal combustion engines containing 15% by volume of MTBE. The research method octane value of this fuel composition was 96.

COMPARATIVE EXAMPLE 1

Example 5 was traced except that the neutralizing tower N was not used. In this modified example, the decomposition of MTBE was caused to occur considerably in the refining tower D and the flow rate of MTBE obtained from the bottom of the refining tower D was as low as 31.3 kg/hr.

Although the present invention has been described in connection with preferred examples thereof, many variations and modifications will now become apparent to those skilled in the art. It is preferred, therefore, that the present invention be limited not by the specific disclosure herein but only by the appended claims.

What is claimed is:

1. A method for preparing a fuel composition for internal combustion engines comprising the steps of:
   (A) allowing isobutylene and methyl alcohol to react with each other by continuously passing an isobutylene-containing hydrocarbon mixture and methyl alcohol through a fixed bed filled with strongly acidic cation-exchange resin particles of 0.2 to 10 mm in mean grain diameter, at a temperature of 0° to 100° C., a pressure of 1 to 50 atmospheres and a liquid space velocity of 0.1 to 50 (1/hr), the molar ratio of isobutylene in said mixture to said methyl alcohol being in the range of 1:0.6 to 1:1.4;
   (B) dividing the effluent from the reaction of step (A) into first and second parts in which the weight ratio of said first part to said second part is in the range from 1:3 to 1:15;
   (C) recycling said second part to the fixed bed in step (A);
   (D) passing said first part through a fixed bed filled with a water-insoluble, solid, particulate acid-neutralizing agent of 0.1 to 10 mm in mean grain diameter, at 0° to 100° C.;
   (E) introducing the neutralized first part into a flashing tower to flash-remove unreacted hydrocarbon and to recover a methyl tert-butyl ether containing mixture from the bottom of said flashing tower; and,
   (F) mixing 2 to 30% by volume of said methyl tert-butyl ether containing mixture with internal combustion fuel.

2. A method for preparing a fuel composition for internal combustion engines comprising the steps of:
   (A) allowing isobutylene and methyl alcohol to react with each other by continuously passing an isobutylene-containing hydrocarbon mixture and methyl alcohol through a fixed bed filled with strongly acidic cation-exchange resin particles of 0.2 to 10 mm in mean grain diameter, at a temperature of 0° to 100° C., a pressure of 1 to 50 atmospheres and a liquid space velocity of 0.1 to 50 (1/hr), the molar ratio of isobutylene in said mixture to said methyl alcohol being in the range of 1:0.6 to 1:1.4;
   (B) dividing the effluent from the reaction step (A) into first and second parts in which the weight ratio of said first part to said second part is in the range from 1:3 to 1:15;
   (C) recycling said second part to the fixed bed in step (A);
   (D) passing said first part through a fixed bed filled with a water-insoluble, solid, particulate acid-neutralizing agent of 0.1 to 10 mm in mean grain diameter, at 0° to 10° C.;
   (E) introducing the neutralized first part into a flashing tower to flash-remove unreacted hydrocarbon and to recover a methyl tert-butyl ether containing mixture from the bottom of said flashing tower;
   (F) distilling said methyl tert-butyl ether-containing mixture with a multistage distillation column to remove an azeotropic mixture of methyl tert-butyl ether and methyl alcohol from the top of said distillation column and to recycle said azeotropic mixture for reuse in step (A), thereby obtaining methyl tert-butyl ether from the bottom of said distillation column; and
   (G) mixing 2 to 30% by volume of said methyl tert-butyl ether containing mixture with internal combustion fuel.

3. The method for preparing a fuel composition as defined in claims 1 or 2, wherein said internal combustion fuel is at least one member selected from the group consisting of alcohols having 1 to 4 carbon atoms, ethers having 4 to 8 carbon atoms and hydrocarbons boiling in the gasoline range.

4. The methods of claims 1 or 2, wherein said molar ratio of isobutylene to said methyl alcohol is in the range of 1:1 to 1:1.3, a liquid space velocity of 0.5–15 (1/hr) is employed in step (A) and a liquid space velocity of 0.1–20 (1/hr) is employed in step (D).

5. The method of claim 4, wherein said neutralizing agent is hydrotalcite.

6. The method of claim 5, wherein said hydrotalcite is a natural hydrotalcite having a molar ratio of magnesium to aluminum of about 3.

7. The method of claim 4, wherein said hydrotalcite is a synthetic hydrotalcite having a molar ratio of magnesium to aluminum of 1–10.